United States Patent
Ibrahim et al.

(10) Patent No.: US 6,232,351 B1
(45) Date of Patent: *May 15, 2001

(54) CO-PROCESSED BOTANICAL PLANT COMPOSITION

(75) Inventors: Nagui Ibrahim, Fountain Valley; Manoj Saraiya, Irving, both of CA (US)

(73) Assignee: Amway Corporation, Ada, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/083,568

(22) Filed: May 22, 1998

(51) Int. Cl.[7] .................................................. A61K 47/00
(52) U.S. Cl. .......................... 514/781; 514/770; 514/783; 514/960; 424/464; 424/465
(58) Field of Search ............................... 514/57, 63, 769, 514/770, 781, 783, 951, 960; 424/464, 465

(56) References Cited

U.S. PATENT DOCUMENTS

| | | | |
|---|---|---|---|
| 3,600,189 | 8/1971 | Raynal | 99/6 |
| 3,639,169 * | 2/1972 | Broeg et al. | 127/29 |
| 4,159,345 | 6/1979 | Takeo et al. | 424/362 |
| 4,327,076 * | 4/1982 | Puglia et al. | 424/38 |
| 4,744,987 | 5/1988 | Mehra et al. | 424/156 |
| 4,929,605 * | 5/1990 | Domet et al. | 514/54 |
| 4,999,200 | 3/1991 | Casillan | 424/480 |
| 5,030,447 * | 7/1991 | Joshi et al. | 424/80 |
| 5,051,261 | 9/1991 | McGinity et al. | 424/464 |
| 5,093,130 * | 3/1992 | Fujii et al. | 424/463 |
| 5,145,695 | 9/1992 | Smith et al. | 426/2 |
| 5,277,910 | 1/1994 | Hidvégi | 424/195.1 |
| 5,441,753 | 8/1995 | McGinley et al. | 426/96 |
| 5,462,761 | 10/1995 | McGinley et al. | 426/573 |
| 5,585,115 | 12/1996 | Sherwood et al. | 424/489 |
| 5,643,591 | 7/1997 | Mehra et al. | 424/408 |
| 5,725,883 * | 3/1998 | Staniforth et al. | 424/489 |
| 5,725,884 * | 3/1998 | Staniforth et al. | 424/489 |
| 5,733,578 * | 3/1998 | Hunter et al. | 424/489 |
| 5,741,524 * | 4/1998 | Staniforth et al. | 424/489 |
| 5,747,067 * | 5/1998 | Augello et al. | 424/464 |
| 5,858,409 | 1/1999 | Karetny et al. | 424/489 |

FOREIGN PATENT DOCUMENTS

| | | |
|---|---|---|
| 0 311 067 A1 * | 4/1989 | (EP) . |
| 0 600 725 A1 * | 6/1994 | (EP) . |
| 11999915 | 7/1970 | (GB) . |
| 57-129655 | 8/1982 | (JP) . |
| 03080054 A2 * | 4/1991 | (JP) . |
| 06227999 | 8/1994 | (JP) . |
| 08322508A2 * | 12/1996 | (JP) . |
| 9001923 * | 3/1992 | (NL) . |
| WO 96/21429 | 7/1996 | (WO) . |
| WO 96/22080 | 7/1996 | (WO) . |
| WO 97/23139 | 7/1997 | (WO) . |
| WO 97/41741 | 11/1997 | (WO) . |
| WO 98/03064 | 1/1998 | (WO) . |

OTHER PUBLICATIONS

Pharmaceutical Dosage Forms and Drug Delivery Systems, edited by Ansel et al., published by Williams and Wilkins, pp. 182–222, 1995.*
PCT International Search Report, PCT/US99/111382 for Amway Corporation, filed May 21, 1999.
Podczeck et al. "The Influence of Particle Size and Shape on the Angle of Internal Friction and the Flow Factor of Unlubricated and Lubricated Powders," *Int. J. of Pharm*, vol. 144:187–194, (1996).*

* cited by examiner

Primary Examiner—Howard C. Lee
(74) Attorney, Agent, or Firm—Brinks Hofer Gilson & Lione

(57) ABSTRACT

A particulate co-processed composition that includes a botanical plant, microcrystalline cellulose and calcium carbonate. The botanical plant is selected from the group consisting of grains, plants, roots, and mixtures thereof. The co-processed composition is particularly useful in the manufacture of vitamins and food supplements.

The co-processed composition is prepared by forming a slurry of the botanical plant, microcrystalline cellulose, and calcium carbonate and then drying the slurry to yield a particulate product.

37 Claims, 1 Drawing Sheet

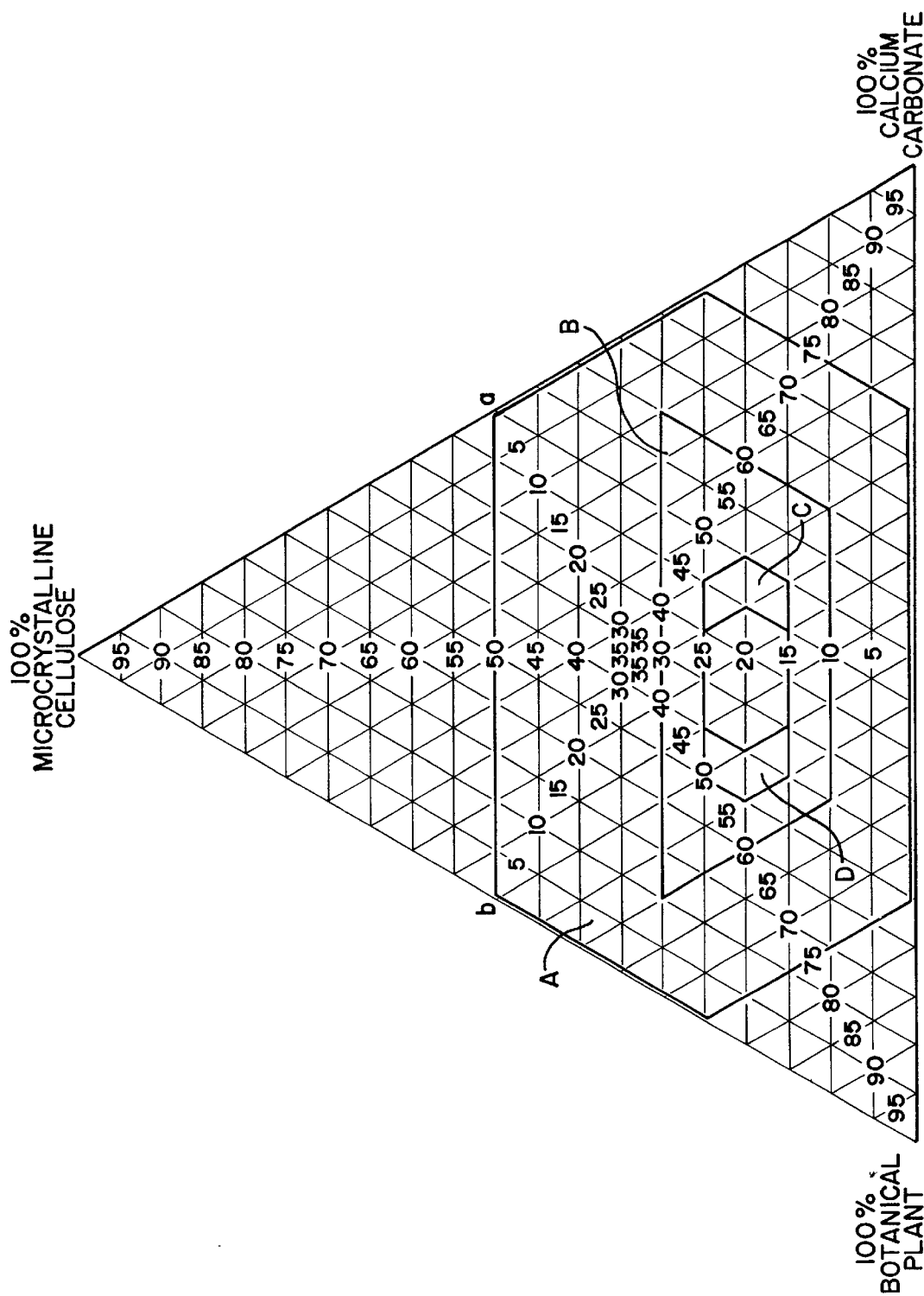

CO-PROCESSED BOTANICAL PLANT COMPOSITION

The present invention relates to a particulate co-processed plant composition that includes a botanical plant, microcrystalline cellulose, and calcium carbonate. The composition is particularly useful in vitamin and nutritional supplement formulations. The present invention is an improvement on the known co-processed microcrystalline cellulose formulations. In the present invention, the botanical plant, microcrystalline cellulose, and calcium carbonate are processed together in an aqueous medium and dried to yield a particulate product.

BACKGROUND OF THE INVENTION

Microcrystalline cellulose finds widespread use as a pharmaceutical excipient because it possesses desirable compressibility characteristics. Microcrystalline cellulose is a purified, partially de-polymerized cellulose that is prepared by treating alpha cellulose, in the form of a pulp manufactured from fibrous plant material, with mineral acids. It is a white, odorless, tasteless, relatively free flowing powder that is insoluble in water, organic solvents, dilute alkalis and dilute acids. U.S. Pat. No. 2,978,446 issued to Battista et al. and U.S. Pat. No. 3,146,168 issued to Baftista describe microcrystalline cellulose and its manufacture; the latter patent concerns microcrystalline cellulose for pharmaceutical applications. Both are incorporated herein by reference in their entirety.

Unfortunately, microcrystalline cellulose is relatively costly to manufacture. This limits its use in price-sensitive formulations like vitamins and nutritional supplements. Thus, a lower cost replacement that has tabletting characteristics similar to those of microcrystalline cellulose is desired.

One solution is proposed by U.S. Pat. No. 5,585,115, which describes a particulate agglomerate of microcrystalline cellulose and from about 0.1–20% silicon dioxide. Another solution is proposed by U.S. Pat. No. 4,744,987, which describes a particulate co-processed microcrystalline cellulose and calcium carbonate in a ratio of 75:25 to 35:65.

Although these proposed solutions may be cheaper than simply using microcrystalline cellulose alone, each still requires a major amount of microcrystalline cellulose. Thus, there is still a need for a product that is suitable for tabletting and that has acceptable compressibility characteristics but contains less microcrystalline cellulose than the co-processed microcrystalline cellulose products in the prior art.

The present invention solves that need by providing a composition that includes three components: a botanical plant, microcrystalline cellulose, and calcium carbonate, a that are co-processed in a manner that produces a particulate product having unexpectedly good performance characteristics, but contains a minor amount of microcrystalline cellulose. For example, the product provides excellent compressibility, flow properties, and rapid disintegration.

Moreover, the composition of the present invention eliminates the need for wet granulation.

SUMMARY OF THE INVENTION

In accordance with the present invention, a novel composition is provided that is useful for nutritional supplements and vitamins. The composition is a particulate co-processed composition that includes a botanical plant, microcrystalline cellulose, and calcium carbonate, with the botanical plant being present in an amount from about 1% to about 75%, the microcrystalline cellulose being present in an amount from about 1% to about 50%, and the calcium carbonate being present in an amount from about 1% to about 75%.

The botanical plant is preferably a natural ingredient suitable for oral ingestion by a human. Preferably, the botanical plant is selected from the group consisting of edible grains, plants, roots, and mixtures thereof. More preferably, the botanical plant is selected from the group consisting of alfalfa, wheat, oat, barley, rice, corn, watercress, parsley, brassica and umbelliferous plants, spinach, spirolina, and mixtures thereof.

The microcrystalline cellulose may be derived from any source. The term "microcrystalline cellulose" as used in the foregoing specification and the appended claims means both the wet cake from a conventional microcrystalline cellulose process and the dried or finished product. The wet cake is material that has not yet been dried and is oftentimes referred to as hydrocellulose. The dried or finished product is commercially available under the tradename EMCO-CEL® from Edward Mendell Co. or as Avicel® from FMC Corp.

The calcium carbonate can be derived from any source such as by precipitation, mining, and harvesting (e.g., from oyster shells).

The three components are intimately associated in the co-processed product and may be present as agglomerates of the three components. The particulate co-processed composition is preferably a spray dried material. Preferably, the particle size of the co-processed product is such that substantially all particles are less than No. 60 sieve (250 $\mu$m) and preferably have an average particle size in the range of from 20 $\mu$m to 150 $\mu$m.

The particulate co-processed composition is prepared by forming a well-dispersed aqueous slurry of the botanical plant, microcrystalline cellulose, and calcium carbonate and then drying by removing water resulting in the particulate co-processed product.

The aqueous well-dispersed slurry of the three components is preferably formed by introducing the microcrystalline cellulose, calcium carbonate, and botanical plant into an aqueous medium, with their addition being in the order mentioned, in amounts that yield a relatively concentrated slurry of at least 1% solids. The aqueous slurry is preferably dried by spray drying to yield the particulate co-processed product.

It is therefore an object of the present invention to provide an oral solid dosage form for one or more active ingredients that is economical to manufacture, maintains its integrity during storage, and possesses excellent disintegration and dissolution properties when exposed, e.g., to gastrointestinal fluid.

The present invention is further directed to a mixture of an active ingredient(s) and the particulate co-processed composition of the present invention. The ratio of active ingredient to the co-processed composition is from about 1:99 to about 99:1, by weight.

The present invention is further directed to a compressed solid dosage form comprising an active ingredient(s) and the novel co-processed composition described herein, wherein the active ingredient(s) and the co-processed composition have been directly compressed into the solid dosage.

It is to be noted that, unless otherwise stated, all percentages stated in this specification and appended claims refer to percentages by weight.

These and other objects, advantages, and features of the present invention will be better understood upon review of the following detailed description.

BRIEF DESCRIPTION OF THE DRAWING

FIG. 1 is a ternary diagram of various embodiments of the co-processed composition of the present invention.

DETAILED DESCRIPTION OF THE INVENTION

The particulate co-processed composition of this invention contains three essential components; a botanical plant, microcrystalline cellulose, and calcium carbonate. Referring to FIG. 1, several areas have been labeled and depict the ranges for each component that may be useful for preparing compositions according to the present invention. The areas labeled A and B depict useful and preferred combinations of each ingredient, respectively. Area C depicts a preferred combination of each ingredient where the calcium carbonate is precipitated or mined. Area D depicts a preferred combination of each ingredient where the calcium carbonate is supplied from oyster shells. It will be apparent that those areas correspond with the following ranges:

| Component | A | B | C | D |
| --- | --- | --- | --- | --- |
| botanical plant | 1–75 | 10–60 | 30–50 | 35–55 |
| microcrystalline cellulose | 1–50 | 10–30 | 15–25 | 15–25 |
| calcium carbonate | 1–75 | 10–60 | 30–50 | 25–45 |

Other ingredients may also be incorporated into the particulate product during its preparation. These are ordinarily present in relatively small amounts, representing less than 20%, and preferably less than 10%, of the total particulate product weight. Such additives may be incorporated to facilitate the co-processing procedure, particularly during the drying step, or to provide enhanced properties for resulting finished products. Examples of additives in these categories are binders, e.g., water-soluble gums like hydroxypropylmethylcellulose, methylcellulose, polyvinylpyrrolidone, etc.; lubricants, e.g., long chain fatty acid esters or salts thereof like palmitic and stearic acids; disintegrants like cross-linked carboxymethylcellulose, starch, etc.; and non-silicon metal oxides, starches, starch derivatives, surfactants, polyalkylene oxides, celluloses, cellulose ethers, cellulose esters and mixtures thereof.

The particulate co-processed product of this invention possesses desirable performance attributes that are not achieved by the corresponding wet granulation of botanical plant, microcrystalline cellulose, and calcium carbonate. The mechanism that occurs during the co-processing procedure required in this invention is not fully understood but appears to yield a particulate product in which the three essential components are in intimate association with each other. This intimate association or admixture of the botanical plant, microcrystalline cellulose, and calcium carbonate, apparently cannot be achieved through wet granulation of these materials, but rather requires that they be co-processed as an aqueous slurry or mixture.

This intimate association of the three components apparently manifests itself in the appearance of particles, containing the botanical plant, microcrystalline cellulose, and calcium carbonate, that result after drying of the slurry.

In simple terms, the process for preparing the particulate product of this invention involves forming a well dispersed aqueous slurry of the botanical plant, microcrystalline cellulose, and calcium carbonate. The relative amounts of the three components are adjusted in the slurry to yield the specific weight ratio desired in the recovered co-processed product. Since the weight ratio of the three components in the particulate co-processed product corresponds closely to that in the precursor well-dispersed slurry, this ratio adjustment is relatively straightforward.

The process of this invention next involves drying the aqueous slurry by removing water from it to yield the particulate co-processed product. Spray drying is the preferred drying means but other drying methods, e.g. flash drying, freeze drying, fluidized bed drying, ring drying, micron drying, tray drying, vacuum drying, radio-frequency drying, or microwave drying, may also be adapted for use in this co-processing step.

The three components used in forming the well dispersed aqueous slurry are the botanical plant, microcrystalline cellulose, and calcium carbonate. The source and nature of these components is not particularly critical.

For example, the botanical plant can be a natural ingredient suitable for oral ingestion by a human. Preferably, the botanical plant is selected from the group consisting of edible grains, plants, roots, and mixtures thereof. More preferably, the botanical plant is selected from the group consisting of alfalfa, wheat, oat, barley, rice, corn, watercress, parsley, spinach, brassica and umbelliferous plants, spirolina, and mixtures thereof. In a preferred embodiment, the botanical plant consists of alfalfa.

The botanical plant material should be finely ground so that substantially all, e.g., greater than about 95%, passes through a 100 mesh screen (i.e., about 250 $\mu$m).

The co-processed composition includes from about 1% to about 75% of the botanical plant, preferably from about 10% to about 60%. The botanical plant is preferably included in an amount from about 30% to about 50%, most preferably about 40%, when the calcium carbonate source is mined or precipitated. The botanical plant is preferably included in an amount from about 35% to about 55%, most preferably about 45%, when the calcium carbonate is derived from oyster shells.

The microcrystalline cellulose used in the composition of the present invention can be the so-called wet-cake or the dried finished product. The wet cake is material which has not yet been dried, to yield a conventional microcrystalline cellulose free-flowing powder product. The wet cake is sometimes referred to as "never dried" or hydrocellulose.

The dried finished microcrystalline cellulose may be prepared by partially depolymerizing cellulose obtained as a pulp from fibrous plant material with dilute mineral acid solutions. Following hydrolysis, the hydrocellulose thereby obtained is purified via filtration and the aqueous slurry may be spray dried to form dry, white odorless, tasteless crystalline powder of porous particles of a broad size distribution. Another method of preparing microcrystalline cellulose is disclosed in U.S. Pat. No. 3,141,875. This patent discloses subjecting cellulose to the hydrolytic action of hydrochloric acid at boiling temperatures so that amorphous cellulosic material can be removed and aggregates of crystalline cellulose are formed. The aggregates are A collected by filtration, washed with water and aqueous ammonia and disintegrated into small fragments, often called cellulose crystallites by vigorous mechanical means such as a blender.

The particle size of the microcrystalline cellulose used in the aqueous slurry is ordinarily that which is encountered in conventional microcrystalline cellulose product, or in its precursor wet cake. No matter how made, microcrystalline cellulose is commercially available in several grades which range in average particle size from 5 to 200 microns. The particle size is desirably such that substantially all particles are less than No. 60 sieve (250 μm) in size.

Specific size requirements for fine particle sizes, if desired, can be met through screening off unwanted coarse material or through conventional wet or dry attrition procedures. Such attrition may also be accomplished with the microcrystalline cellulose in the aqueous slurry. These size reduction procedures are ordinarily not required with microcrystalline cellulose as is now commercially produced.

The microcrystalline cellulose is present in the co-processed composition in an amount less than about 50%, typically from about 1% to about 50%, preferably from about 10% to about 30%, more preferably from about 15% to about 25%, and most preferably about 20%.

The calcium carbonate ($CaCO_3$) used in this invention may be from any known source. For example, without limitation, the calcium carbonate can be from a precipitated material, mined material, or harvested material such as oyster shells. Precipitated calcium carbonate may be desirable since it is ordinarily more pure than ground calcium carbonate and typically has a finer particle size. Ground calcium carbonate may nevertheless be used as a source with satisfactory results. To provide a more natural end product, calcium carbonate from oyster shells is preferred.

The particulate calcium carbonate is preferably finer in particle size than the particulate microcrystalline cellulose with which it is co-processed. Extremely fine particle size calcium carbonate is more readily combined in intimate association with the microcrystalline cellulose during co-processing of the three components.

Calcium carbonate sizing is preferably such that substantially all particles are less than 30 μm in size and, more preferably, less than 10 μm. Average particle size of the calcium carbonate is desirably less than 5 μm and, more preferably, is less than 2 μm.

The calcium carbonate may be included in the co-processed composition of the present invention in an amount from about 1% to about 75%, preferably from about 10% to about 60%. When the calcium carbonate source is mined or precipitated, it is preferably included in an amount from about 30% to about 50%, most preferably about 40%. When the calcium carbonate is derived from oyster shells, the botanical plant is preferably included in an amount from about 25% to about 45%, most preferably about 35%.

Both microcrystalline cellulose and calcium carbonate are substantially insoluble in water. Consequently, the particle size of the material present in the well dispersed aqueous slurry is directly related to the sizing of the two components introduced to the slurry; i.e., there is no appreciable dissolution of either of these two components in the aqueous slurry.

The aqueous slurry of these three components may be prepared in any of several ways. The three components may both be introduced into a single aqueous medium, or each may be introduced separately into separate aqueous media which are then combined, or other analogous procedures may be devised.

One procedure involves dispersing the microcrystalline cellulose alone into an aqueous solution, preferably water. Once the microcrystalline cellulose is well-dispersed in the aqueous slurry, the appropriate amount of calcium carbonate may be added, in dry form, with mixing being continued during its addition. The exact amount of calcium carbonate to be added depends on the microcrystalline cellulose content of the slurry, the amount of botanical plant to be added, and the ratio of the three components desired in the co-processed product.

Once the microcrystalline cellulose and calcium carbonate are well-dispersed in the aqueous slurry, the desired amount of botanical plant may be added, with continued mixing. The amount of botanical plant to be added depends on the microcrystalline cellulose and calcium carbonate content of the slurry and the ratio of the three components desired in the co-processed product.

Water may also be added if a more dilute slurry is desired, but this is usually not required. The aqueous slurry containing the three components should be well mixed to assure uniform dispersion of the components throughout the aqueous medium. This is necessary to provide for a uniform, consistent component ratio in the particulate product, prepared by drying the aqueous slurry.

The total solids content of the aqueous slurry should be at least 1%, based on the total slurry weight, and preferably should be at least 20% solids, more preferably. 35% solids. The higher solids content levels are desirable since the amount of water that must be removed during the drying step is accordingly reduced. Consequently, the solids content of the aqueous slurry will be as high as can be achieved and yet allow efficient processing conditions. The upper limit on solids content in the aqueous slurry is typically determined by the operating constraints of the drying apparatus used.

The temperature of the aqueous slurry is not critical. Ambient temperatures, of from about 10–25° C., are generally preferred. Higher slurry temperatures may be used, and these may be desirable with certain types of drying equipment.

The drying of the well-dispersed aqueous slurry is preferably accomplished by spray drying of the slurry. Conventional spray drying equipment may be used, and operating procedures that are familiar to those experienced in the spray drying art are applicable to the spray drying step of this process. Drier (drier gas) outlet temperature is ordinarily used to control the residual moisture level obtained in the co-processed particulate product. In a spray drying procedure, drier outlet temperatures are ordinarily in the range of about 40–100° C. Corresponding drier inlet temperatures are higher, ordinarily in the range of about 90–300° C.

Moisture levels of about 0.5% to about 10% water are desired in the co-processed dried composition and moisture levels of about 1% to about 8% are preferred, with a level of from about 1.5% to about 4% being more preferred and about 1.8% being most preferred.

The co-processed product recovered from the drying operation is a free-flowing particulate solid, that typically has a fine granular powder appearance. The particle size of the product is a function of the particle size of the botanical plant, microcrystalline cellulose, and calcium carbonate in the aqueous slurry and, more importantly, of the drying conditions employed for removing water from the slurry. The particulate co-processed product should have a particle size such that substantially all are less than No. 60 sieve (250 μm). The average particle size of the particulate material is preferably in the range of from about 20 μm to 150 μm and more preferably is in the range of from about 30 μm to 100 μm with a range of about 50 μm to about 90 μm being most preferred.

The exact relationship of the components of the composition after co-processing is not presently understood;

however, for purposes of description the co-processed particles are described herein as including an agglomerate of microcrystalline cellulose, calcium carbonate and botanical plant in intimate association with each other. By "intimate association," it is meant that each component has in some manner been integrated with the other components, as opposed to a chemical interaction of the ingredients. The term "intimate association" is therefore deemed for purposes of the present description as being synonymous with "integrated" or "united." The co-processed particles, however, are not necessarily uniform or homogeneous.

The bulk density (loose) of the co-processed product is typically in the range of about 0.4 to about 0.6 g/cm$^3$. Microcrystalline cellulose ordinarily exhibits a loose bulk density of about 0.28–0.30 g/cm$^3$.

The particulate co-processed product of this invention, besides being economical, has several desirable properties that make it particularly well-suited for use in direct compression tabletting applications such as those typically used in making vitamins. For example, the compressibility of this co-processed product compares favorably with that of commercially available microcrystalline celluloses. Compressibility is typically measured as the profile, or shape, of the plot of tablet hardness vs. tablet compression force.

The novel co-processed composition of the invention is free-flowing and directly compressible. Accordingly, the co-processed composition of the present invention may be mixed in the desired proportion with an active agent and optional lubricant, and then directly compressed into solid dosage forms.

The active agent(s) that may be combined with the novel co-processed composition into solid dosage forms include herbs, herbal extracts, fruits, vegetables, extracts from fruits and/or vegetables, vitamins, antioxidants, proteins, minerals, fatty acids, lecithin, honey, therapeutic agents, and the like.

The solid formulations of the invention may also include other locally active agents, such as flavorants and sweeteners. Generally any flavoring or food additive such as those described in *Chemicals Used in Food Processing*, pub 1274 by the National Academy of Sciences, pages 63–258 may be used. Generally, the final product may include from about 0.1% to about 5% by weight flavorant.

The tablets of the present invention may also contain effective amounts of coloring agents, (e.g., titanium dioxide, FD & C and D & C dyes; see the Kirk-Othmer Encyclopedia of Chemical Technology, Vol. 5, pp. 857–884, hereby incorporated by reference), stabilizers, binders, odor controlling agents, and preservatives.

The following examples illustrate, but do not limit, the present invention. Unless otherwise indicated, all parts and percentages are by weight.

EXAMPLE 1

Tablets were prepared by blending a co-processed alfalfa composition according to the present invention with other excipients and compressing the blend to form tablets. An iron dissolution test was performed according to USP 23-NF 18 on a tablet. It was found that the tablet exhibited 100% iron dissolution after 60 minutes and exhibited 90% iron dissolution after 10 minutes.

Commercially available tablets under the brand name Triple X from Nutrilite contain an alfalfa base and are made using a wet granulation process. An iron dissolution test was performed according to USP 23-NF 18 on a Triple X tablet. It was found that the tablet exhibited 56% iron dissolution after 60 minutes.

These results demonstrate that a tablet that incorporates the co-processed botanical composition of the present invention not only achieves complete dissolution but does so much more rapidly than a tablet prepared using a conventional wet granulation process.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A direct tabletting agent comprising dried particulates of co-processed:
    a. plant;
    b. microcrystalline cellulose; and
    c. calcium carbonate,
wherein the three components are intimately associated with each other.

2. The agent of claim 1, wherein the particulates are a spray-dried co-processed plant, microcrystalline cellulose, and calcium carbonate.

3. The agent of claim 1 wherein the plant is present in an amount from about 1% by weight to about 75% by weight, the microcrystalline cellulose is present in an amount from about 1% by weight to about 50% by weight and the calcium carbonate is present in an amount from about 1% by weight to about 75% by weight.

4. The agent of claim 1 wherein the plant comprises a part of a plant selected from the group consisting of grains, plants, roots and mixtures thereof.

5. The agent of claim 4 wherein the plant is selected from the group consisting of alfalfa, wheat, oat, barley, rice, corn, watercress, parsley, spinach, brassica and umbelliferous plants, spirolina, and mixtures thereof.

6. The agent of claim 1 wherein substantially all of the particulates are less than 250 μm in size.

7. The agent of claim 1 wherein the particulates have an average particle size in the range of from 20 μm to 150 μm.

8. The agent of claim 1 wherein the particulates have a moisture content of from about 1% by weight to about 10% by weight.

9. The agent of claim 1, wherein the composition has a bulk density from about 0.4 g/ml to about 0.6 g/ml.

10. The agent of claim 1, wherein the agent further comprises an additive selected from the group consisting of non-silicon metal oxides, starches, starch derivatives, surfactants, polyalkylene oxides, celluloses, cellulose ethers, cellulose esters and mixtures thereof, wherein the additive is present in an amount less than about 20% by weight.

11. A composition comprising
    a. from about 1% by weight to about 99% by weight of a particulate agglomerate that comprises from about 1% by weight to about 75% by weight of a plant co-processed with microcrystalline cellulose and calcium carbonate, wherein the plant, microcrystalline cellulose, and calcium carbonate are in intimate association with each other, and
    b. from about 99% by weight to about 1% by weight of an active ingredient.

12. The composition of claim 11 wherein the active ingredient is different than the plant and is selected from the group consisting of herbs, extracts of herbs, fruits, fruit extracts, vegetables, vegetable extracts, vitamins, minerals, antioxidants, proteins, therapeutic agents, and mixtures thereof.

13. The composition of claim 12 wherein the active ingredient is selected from the group consisting of minerals and vitamins.

14. The composition of claim 12 wherein the plant is selected from the group consisting of alfalfa, wheat, oat, barley, rice, corn, watercress, parsley, spinach, brassica and umbelliferous plants, spirolina, and mixtures thereof.

15. The composition of claim 14 wherein the plant is alfalfa.

16. The composition of claim 14 wherein the microcrystalline cellulose is present in an amount from about 1% by weight to about 50% by weight and the calcium carbonate is present in an amount from about 1% by weight to about 75% by weight.

17. A process for preparing a direct tablefting agent that comprises
   a. forming a well-dispersed aqueous slurry that includes a plant, microcrystalline cellulose, and calcium carbonate, and
   b. drying the aqueous slurry by removing water.

18. The process of claim 17 wherein the aqueous slurry is dried by spray drying.

19. The process of claim 18 wherein the plant is selected front the group consisting of alfalfa, wheat, oat, barley, rice, corn, watercress, parsley, spinach, brassica and umbelliferous plants, spirolina, and mixtures thereof.

20. The process of claim 17 wherein the plant is present in amount from about 1% by weight to about 75% by weight, the microcrystalline cellulose is present in an amount from about 1% by weight to about 50% by weight and the calcium carbonate is present in an amount from about 1% by weight to about 75% by weight.

21. A direct tabletting agent comprising dried particulates of co-processed:
   a. plant;
   b. microcrystalline cellulose; and
   c. calcium carbonate intimately associated with each other,
wherein the plant is present in an amount from about 20% by weight to about 75% by weight.

22. The agent of claim 21, wherein the microcrystalline cellulose is present in an amount from about 1% by weight to about 50% by weight and the calcium carbonate is present in an amount from about 1% by weight to about 75% by weight.

23. The agent of claim 21, wherein the plant is selected from the group consisting of alfalfa, wheat, oat, barley, rice, corn, watercress, parsley, spinach, brassica and umbelliferous plants, spirolina, and mixtures thereof.

24. The agent of claim 21, wherein substantially all of the particulates are less than 250 μm in size.

25. The agent of claim 21, wherein the agent further comprises an additive selected form the group consisting of non-silicon metal oxides, starches, starch derivatives, surfactants, polyalkylene oxides, celluloses, cellulose ethers, cellulose esters and mixtures thereof, wherein the additive is present in an amount less than about 20% by weight.

26. A direct tabletting agent comprising:
   a. from about 1% by weight to about 99% by weight of a particulate agglomerate that comprises from about 20% by weight to about 75% by weight of a plant co-processed with microcrystalline cellulose and calcium carbonate, wherein the plant, microcrystalline cellulose, and calcium carbonate are in intimate association with each other, and
   b. from about 99% by weight to about 1% by weight of an active ingredient.

27. The agent of claim 26, wherein the active ingredient is different than the plant and is selected from the group consisting of herbs, extracts of herbs, fruits, fruit extracts, vegetables, vegetable extracts, vitamins, minerals, antioxidants, proteins, therapeutic agents, and mixtures thereof.

28. The agent of claim 26, wherein the plant is alfalfa.

29. A process for preparing a direct tabletting agent that comprises
   a. forming a well-dispersed aqueous slurry comprising plant in an amount from about 20% by weight to about 75% by weight, microcrystalline cellulose, and calcium carbonate, and
   b. drying the aqueous slurry by removing water.

30. The process of claim 29, wherein the aqueous slurry is dried by spray drying.

31. An oral solid dosage form comprising dried particulates of co-processed:
   a. plant;
   b. microcrystalline cellulose; and
   c. calcium carbonate,
wherein the three components being intimately associated with each other.

32. The oral solid dosage form of claim 31 wherein the plant is present in an amount from about 1% by weight to about 75% by weight, the microcrystalline cellulose is present in an amount from about 1% by weight to about 50% by weight and the calcium carbonate is present in an amount from about 1% by weight to about 75% by weight.

33. The oral solid dosage form of claim 31 wherein the plant is selected from the group consisting of alfalfa, wheat, oat, barley, rice, corn, watercress, parsley, spinach, brassica and umbelliferous plants, spirolina, and mixtures thereof.

34. The oral solid dosage form of claim 31 further comprising an additive selected from the group consisting of non-silicon metal oxides, starches, starch derivatives, surfactants, polyalkylene oxides, celluloses, cellulose ethers, cellulose esters and mixtures thereof, wherein the additive is present in an amount less than about 20% by weight.

35. The oral solid dosage form of claim 31 wherein the oral dosage form is a tablet.

36. An oral solid dosage comprising
   a. from about 1% by weight to about 99% by weight of a particulate agglomerate that comprises from about 1% by weight to about 75% by weight of a plant co-processed with microcrystalline cellulose and calcium carbonate, wherein the botanical plant, microcrystalline cellulose, and calcium carbonate are in intimate association with each other, and
   b. from about 99% by weight to about 1% by weight of an active ingredient.

37. The oral solid dosage form of claim 36 wherein the oral dosage form is a tablet.

* * * * *